(12) United States Patent
Grams et al.

(10) Patent No.: US 6,498,252 B1
(45) Date of Patent: Dec. 24, 2002

(54) PYRIMIDINE-2,4,6-TRIONE DERIVATIVES, PROCESSES FOR THEIR PRODUCTION AND PHARMACEUTICAL AGENTS CONTAINING THESE COMPOUNDS

(75) Inventors: Frank Grams, Neuenburg-Zienken (DE); Hans-Willi Krell, Penzberg (DE); Herbert Leinert, Heppenheim (DE); Ernesto Menta, Cernusco sul Naviglio MI (IT); Gerd Zimmermann, Linkenheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/675,935

(22) Filed: Sep. 29, 2000

(30) Foreign Application Priority Data

Oct. 1, 1999 (EP) .............................. 99119506

(51) Int. Cl.⁷ ...................... C07D 403/04; C07D 403/14
(52) U.S. Cl. ....................... 544/295; 544/296
(58) Field of Search ................... 544/295, 296

(56) References Cited

U.S. PATENT DOCUMENTS

| | | | |
|---|---|---|---|
| 4,595,700 A | 6/1986 | Donald, et al. | 514/616 |
| 6,110,924 A | 8/2000 | Bosies et al. | 544/295 |

FOREIGN PATENT DOCUMENTS

| | | |
|---|---|---|
| EP | 320118 | 6/1989 |
| EP | 489577 | 6/1992 |
| EP | 497192 | 8/1992 |
| EP | 0869947 | 7/1997 |
| WO | WO 90/05719 | 5/1990 |
| WO | WO 92/09563 | 6/1992 |
| WO | WO 96/15096 | 5/1996 |
| WO | WO 97/20824 | 6/1997 |

OTHER PUBLICATIONS

D.E. Levy, et al., Emerging Drugs, vol. 2 pp. 205–230 (1997).
M. Whittaker, et al., Opin. Drug Discovery Dev. (1998) vol. 1(2), pp. 157–164.

Primary Examiner—John M. Ford
(74) Attorney, Agent, or Firm—George W. Johnston; Robert A. Silverman

(57) ABSTRACT

Compounds of formula I

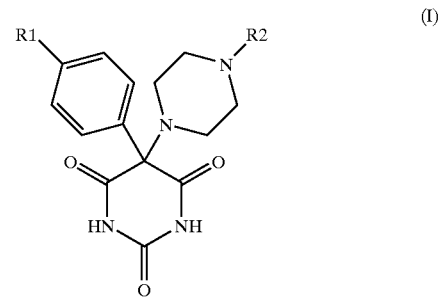

in which
$R_1$ represents a substituted or unsubstituted phenoxy, phenylthio, phenylsulfinyl, phenylsulfonyl, phenylamino or phenylmethyl residue, and
$R_2$ represents an optionally substituted aryl or heteroaryl residue, with metallo-proteinase inhibitor activity.

23 Claims, No Drawings

PYRIMIDINE-2,4,6-TRIONE DERIVATIVES, PROCESSES FOR THEIR PRODUCTION AND PHARMACEUTICAL AGENTS CONTAINING THESE COMPOUNDS

FIELD

This invention relates to derivatives of 5,5-disubstituted pyrimidine-2,4,6-triones. These compounds show a marked antitumor and antimetastatic activity.

BACKGROUND

In normal tissue there is an equilibrium between synthesis and degradation. Extracellular matrix is degraded by proteinases which belong to at least three groups of matrix metalloproteinases. These are the collagenases, gelatinases and stromelysins. Normally there are specific inhibitors for these catabolic enzymes such as $\alpha_2$ macroglobulines and TIMP (=tissue inhibitor of metalloproteinases (MMP)) so that an excessive degradation of extracellular matrix does not occur. Adamalysins are a related group of proteinases. A prominent member of the adamalysins is TACE (TNF-α-converting enzyme).

At least 17 different and yet highly homologous MMP species have been characterized, including the interstitial fibroblast collagenase (MMP-1, HFC), the neutrophil collagenase (MMP-8, HNC), two gelatinases, stromelysins (such as HSL-1) and HPUMP (for a recent review, see Birkedal-Hansen, H., Moore, W. G. I., Bodden, M. K., Windsor, L. J., Birkedal-Hansen; B., DeCarlo, A., Engler, J. A., Critical Rev. Oral Biol.Med. (1993) 4, 197–250. These proteinases share a number of structural and functional features but differ somewhat in their substrate specificity. Only HNC and HFC are capable of cleaving type I, II and III native triple-helical collagens at a single bond with the production of fragments ¾ and ¼ of the native chain length. This lowers the collagen melting point and makes them accessible to further attack by other matrix degrading enzymes.

However, the uncontrolled excessive degradation of this matrix is a characteristic of many pathological states such as e.g. in the clinical picture of rheumatoid arthritis, osteoarthritis and multiple sclerosis, in the formation of tumor metastases, corneal ulceration, inflammatory diseases and invasion and in diseases of bone and teeth.

It can be assumed that the pathogenesis of these clinical pictures can be favourably influenced by the administration of matrix metalloproteinase inhibitors. In the meantime a number of compounds are known from the literature (see e.g. the review article of D. E. Levy, A. M. Ezrin Emerging Drugs 2,205–230 (1997), M. Whittaker, P. Brown, Curr. Opin. Drug Discovery Dev. (1998), 1(2), 157–164. or are described in the patent literature, mainly with a hydroxamic acid residue, a thiol or phosphine group as a zinc binding group (see e.g. WO-A-9209563 by Glycomed, EP-A-497 192 by Hoffmann-LaRoche, WO-A-9005719 by British Biotechnology, EP-A-489 577 by Celltech, EP-A-320 118 by Beecham, U.S. Pat. No. 459 5700 by Searle, WO 97/20824 by Agouron Pharmaceuticals, WO 96/15096 by Bayer Corporation among others).

Some of these compounds show a high activity as inhibitors of matrix metalloproteinases but their oral availability is very low. Also such compounds often show broad spectrum inhibition of metalloproteinases which may be associated to undesired side-effects and toxicity.

Pyrimidine-2,4,6-trione derivatives have been described in EP0869947 generically as inhibitors of matrix metalloproteinases. However, there is still a high need for new compounds having low toxicity, no side-effects and a marked inhibitory activity against metallo-proteinases, especially as candidates for a chronic treatment against tumor growth and metastasis.

It has now been found that the claimed pyrimidine-2,4, 6-trione derivatives have improved activity as matrix metallo-proteinase inhibitors over the compounds claimed in EP0869947 and also show good oral availability.

BRIEF SUMMARY OF THE INVENTION

The present invention concerns compounds of the formula I

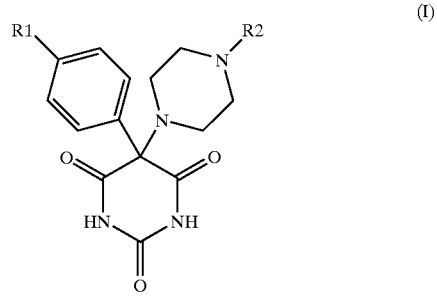

in which

R$_1$ represents a phenyl, phenoxy, phenylthio, phenylsulfmyl, phenylsulfonyl, phenylamino or phenylmethyl residue, wherein the phenyl moiety is unsubstituted or substituted by one or more halogen atoms, hydroxy, C$_1$–C$_6$ alkoxy, C$_1$–C$_6$ alkyl cyano, or nitro groups, and R$_2$ represents an unsubstituted or substituted aryl or hetaryl group.

When the phenyl moiety of R$_1$ is a substituted phenyl moiety, it is preferred that there are one or two substituents in the para and/or meta positions.

The present invention also encompasses pharmaceutically acceptable salts or prodrugs of the compounds of formula I as well as the use of these compounds to produce pharmaceutical agents.

It has now been found that the pyrimidine-2,4,6-trione derivatives of the present invention, have improved activity as matrix metallo-proteinase inhibitors over the compounds claimed in EP0869947 and also show good oral availability.

DETAILED DESCRIPTION OF THE INVENTION

The aryl group of R2 consists of a phenyl ring. The hetaryl group is a cyclic unsaturated or saturated ring system consisting of 5 to 7 ring atoms which can be selected from one or more carbon, nitrogen, oxygen or sulfur atoms. Preferred are electron deficient hetaryl residues such as the nitrogen containing 6 membered rings like pyridines, pyrimidines, pyrazines or 1,3,5-triazines or its N-oxides. Most preferred are the hetaryl residues pyrimidinyl or pyrazinyl.

The aryl or hetaryl rings may be substituted by one or more substituents selected from halogen, hydroxy, alkoxy, amino, dialkylamino, cyano, lower alkyl, lower alkenyl, lower alkinyl, lower acyl, lower alkylthio, lower alkylsulfonyl, lower alkylaminocarbonyl, aminocarbonyl, SO$_2$NR$_3$R$_4$, nitro, lower alkoxycarbonyl, carboxy, wherein R3 and R4, which can be the same or different represent hydrogen; C$_1$–C$_6$ alkyl, straight chained or branched, which can be substituted one or several times by OH, N(CH$_3$)$_2$ or which can be interrupted by oxygen, or represent CO R$_5$, wherein R$_5$ is an alkyl group which can be substituted by NH$_2$. Preferred are substitutions in para and/or meta position by one to two of the above listed substituents.

Lower alkyl in residue $R_2$ as such or in combinations with other residues denotes $C_1$–$C_6$-alkyl, preferred are methyl, ethyl, propyl, isopropyl or tert.-butyl.

Lower alkenyl denotes $C_2$–$C_6$ alkenyl, preferably allyl or pentadienyl. Lower alkinyl denotes $C_2$–$C_6$ alkinyl, preferably propargyl.

Lower acyl in the residue $R_2$ above all denotes —C(O)—$C_1$–$C_6$-alkyl or —C(O)H, preferred for an acetyl group.

The alkyl residues in $R_2$, can optionally be interrupted once or several times by heteroatoms (O, S, NH).

Halogen is understood as fluorine, chlorine, bromine, iodine, preferably chlorine or bromine.

If compounds of the formula I contain one or several asymmetric carbon atoms, the optically active compounds of the formula I are also a subject matter of the present invention.

Compounds of the formula I can be synthesized by well-known processes preferably in that compounds of the formula II

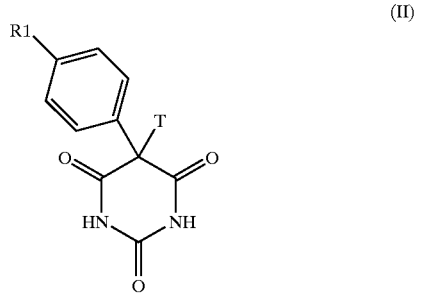

(II)

in which $R_1$ has the above-mentioned meaning and T represents a leaving group such as Hal or $OSO_2R_3$ Hal denoting chlorine, bromine or iodine and $R_3$, denoting an aryl or a methyl residue, are reacted with a compound of the formula III

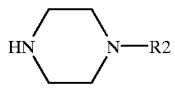

(III)

in which $R_2$ has the meaning stated above and optionally converted into pharmaceutically acceptable salts.

Compounds of the formula II can be synthesized by analogy to known literature procedures. Thus for example pyrimidine-2,4,6-triones brominated in the 5-position can be synthesized by reacting the appropriate bromomalonic acid dialkyl esters with urea (e.g. Acta Chim. Acad. Sci. Hung. 107 (2), 139 (1981)). The corresponding brominated or chlorinated compounds of the formula II can be obtained by reacting pyrimidine-2,4,6-triones substituted by $R_1$-Phenyl in the 5-position with bromine (analogous to J. Prakt. Chemie 136, 329 (1933) or J. Chem. Soc. 1931, 1870) or sulfuryl chloride (J. Chem. Soc. 1938, 1622) or N-bromosuccinimide or similar brominating agents. Such procedures are also described in EP0869947.

Amines of the formula III are commercially available or are usually known in the literature or in analogy to the described methods in the experimental part.

Pyrimidine-2,4,6-triones of formula II with T representing hydrogen can be prepared according to known methods by reacting malonic acid esters with urea (see for example J. Med. Chem. 10, 1078 (1967) or Helvetica Chim. Acta 34, 459 (1959), Pharmacie 38 (1), 65 (1983)) or EP0869947. The reactions are usually carried out in alcohols such as methanol, ethanol or butanol in the presence of an appropriate sodium alcoholate at temperatures between 40° C. and 100° C.

The malonic acid esters which are needed for the preparation of pyrimidine-2,4,6-triones are known from the literature or can be produced according to processes known from the literature. A convenient process for the preparation of malonic acids where $R_1$ has the above mentioned meaning is described in the following scheme:

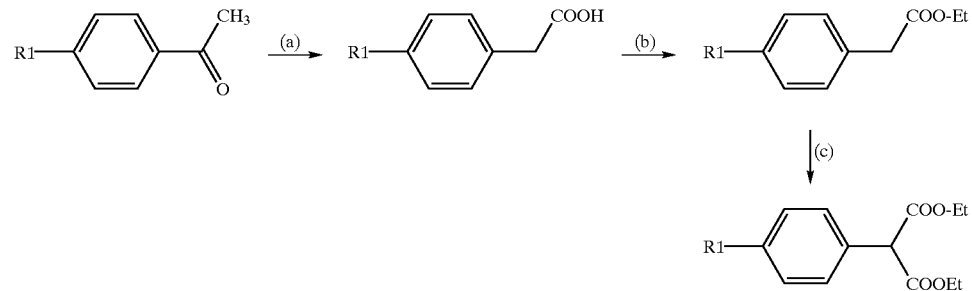

(a) Willgerodt-Kindler reaction
 1. sulfur, morpholine
 2. $H_2SO_4$
(b) esterification
(c) Dimethylcarbonate, NaH Examples for these reactions can be found in Houben-Weyl Vol E5/2, J. Org. Chem. 46, 2999 (1981) and Arch. Pharm. 323, 579 (1990).

Compounds of the formula I can contain one or several chiral centres and can then be present in a racemic or in an optically active form. The racemates can be separated according to known methods into the enantiomers. Preferably diastereomeric salts which can be separated by crystallization are formed from the racemic mixtures by reaction with an optically active acid such as e.g. D- or L-tartaric acid, mandelic acid, malic acid, lactic acid or camphorsulfonic acid or with an optically active amine such as e.g. D- or L-α-phenyl-ethylamine, ephedrine, quinidine or cinchonidine.

Alkaline salts, earth alkaline salts like Ca or Mg salts, ammonium salts, acetates or hydrochlorides are mainly used as pharmaceutically acceptable salts which are produced in the usual manner e.g. by titrating the compounds with inorganic or organic bases or inorganic acids such as e.g. sodium hydroxide, potassium hydroxide, aqueous ammonia, $C_1$–$C_4$-alkyl-amines such as e.g. triethylamine or hydrochloric acid. The salts are usually purified by reprecipitation from water/acetone.

The compounds of formula I and salts thereof according to the invention can be administered enterally or parenterally in a liquid or solid form. In this connection all the usual forms of administration come into consideration such as for example tablets, capsules, coated tablets, syrups, solutions, suspension etc. Water which contains additives such as stabilizers, solubilizers and buffers that are usual in injection solutions is preferably used as the injection medium.

Such additives are e.g. tartrate and citrate buffer, ethanol, complexing agents (such a ethylenediaminetetra-acetic acid and non-toxic salts thereof), high-molecular polymers (such as liquid polyethylene oxide) to regulate viscosity. Liquid carrier substances for injection solutions have to be sterile and are preferably dispensed into ampoules. Solid carrier substances are e.g. starch, lactose, mannitol, methylcellulose, talcum, highly dispersed silicic acids, higher molecular fatty acids (such as stearic acid), gelatins, agar-agar, calcium phosphate, magnesium stearate, animal and vegetable fats, solid high-molecular polymers (such as polyethylene glycols); suitable preparations for oral application can optionally also contain flavourings and sweeteners.

The dosage depends on various factors such as manner of administration, species, age and/or individual state of health. The doses to be administered daily are about 10–1000 mg/human, preferably 100–500 mg/human and can be taken singly or distributed over several administrations.

Prodrugs of the compounds of the invention are such which are converted in vivo to the pharmacological active compound. The most common prodrugs are carboxylic acid esters.

EXAMPLE 1

5-(4-(4-Chloro-phenoxy)-phenyl)-5-(4-pyrimidine-2-yl-piperazine)-pyrimidine-2,4,6-trione A) 1-(4-(4-Chloro-phenoxy)-phenyl-ethanone 4-Fluoro-acetophenone (24.4 g) was dissolved in dimethylformamide (180 ml), 4-Chlorophenol (22.8 g) and potassium carbonate (29.5 g) are added. The mixture was heated with stirring for 7 hrs. under reflux. After cooling the mixture was diluted with water and extracted with methylene chloride. The organic phase was washed with water, dried and evaporated to yield 38 g of a crystalline solid. M.p.66–68° C.

B) 2-(4-(4-Chloro-phenoxy)-phenyl)-morpholine-4-yl-ethanthione 12.4 g of the product obtained by the above procedure were mixed with sulfur (4 g) and morpholine (8.8 ml). The mixture was heated to 150° C. for 2 hrs, cooled in an ice bath and treated with ethanol(20 ml) for 30 minutes. The precipitated crystals were collected and recrystallized from ethanol to yield 13 g of the title compound. M.p. 104–105° C.

C) (4-(4-Chloro-phenoxy)-phenyl)-acetic acid 10.4 g of the compound prepared in step B were heated together with 50% sulfuric acid (200 ml) to 130° C. for 8 hrs. After cooling to room temperature, the reaction mixture was diluted with water (300 ml) and extracted with ethyl acetate. The organic phase was washed with water and subsequently extracted with 2N sodium carbonate solution. The aqueous phase was acidified with dilute hydrochloric acid, ethyl acetate was added, the organic phase was separated, dried and evaporated to yield 5.1 g of a brownish residue. m.p.98–100° C.

D) (4-(4-Chloro-phenoxy)-phenyl)-acetic acid methyl ester 5.1 g of the product from step C were dissolved in methanol (50 ml). The solution was cooled to −10° C. and treated with thionyl chloride (3 ml) and subsequently heated under reflux for 1 hour. The reaction mixture was evaporated and the residue dissolved in ether. The ether phase was washed with water, dried and evaporated to yield 5.1 g of a reddish brown oil.

E) 2-(4-(4-Chloro-phenoxy)-phenyl)-malonic acid dimethyl ester

A suspension of sodium hydride (350 mg) in dimethyl carbonate (10 ml) was treated at room temperature with the product obtained in step D. The mixture was heated to 90° C. for 1 hour, cooled and poured into ice water and extracted with methylene chloride. The extract was dried and evaporated to yield 5.7 of the title compound as an oil.

F) 5-(4-(4-Chloro-phenoxy)-phenyl)-pyrimidine,2,4,-6-trione

Sodium (800 mg) was dissolved in ethanol (80 ml). To this solution was added urea (1.65 g) and a solution of the compound obtained above in ethanol (5.5 g). The mixture was heated for 3 hours under reflux, cooled to room temperature, treated with ice water (100 ml) and acidified with dilute hydrochloric acid. The precipitate was collected, washed with water and dried to yield 5 g of the title compound. M.p. 257–258° C.

G) 5-Bromo 5-(4-(4-Chloro-phenoxy)-phenyl)-pyrimidine, 2,4,-6-trione

A suspension of the compound obtained in step F (6.3 g), N-bromo-succinimide (4.1 g) and dibenzoylperoxide (100 mg) in carbon tetrachloride (120 ml) was stirred for 3 hours at room temperature. The mixture was evaporated , the residue extracted with ethyl acetate. The organic phase was dried and evaporated to yield 7.5 g of the title compound as a thick oil.

H) 5-(4-(4-Chloro-phenoxy)-phenyl)-5-(4-pyrimidine-2-yl-piperazine)-pyrimidine-2,4,6-trione A solution of the compound from step G (410 mg) in methanol (5 ml) was treated with N-(pyrimidin-2-yl)-piperazin (330 mg). The mixture was stirrred for 24 hours. The residue obtained after evaporation of the reaction mixture was chromatographed on silica gel with methylenchloride/methanol 5% as eluent. Pooling of the relevant fractions yields 410 mg of the title compound as an amorphous solid identified by mass spectroscopy: m/e 492.

EXAMPLE 2

5-[4-Chloro-phenoxy)-phenyl]-5-(2,3,5,6-tetrahydro-[1,2']bipyrazinyl-4-yl)-pyrimidine-2,4,6-trione The title compound was prepared by analogy to example 1 step H using 330 mg 1-(pyrazin-2yl)-piperazine instead of the N-(pyrimidin-2-yl)-piperazine yielding 460 mg of the title compound as an amorphous product identified by mass spectrometry: m/e: 492.

EXAMPLE 3

The following compounds were prepared using the procedures of example 1 replacing 4-chlorophenol by the corresponding phenols. The final products were identified by mass spectrometry

| No. | Chemical name | m/e |
|---|---|---|
| 1 | 5-[4-(3,4-Dichloro-phenoxy)-phenyl]-5-(4-pyrimidin-2-yl-piperazin-1-yl)-pyrimidine-2,4,6-trione | 526 |
| 2 | 5-[4-(3,4-Dichloro-phenoxy)-phenyl]-5-(2,3,5,6-tetrahydro-[1,2']bipyrazinyl-4-yl)-pyrimidine-2,4,6-trione | 526 |
| 3 | 5-[4-(2,4-Dichloro-phenoxy)-phenyl]-5-(4-pyrimidin-2-yl-piperazin-1-yl)-pyrimidine-2,4,6-trione | 526 |
| 4 | 5-[4-(2,4-Dichloro-phenoxy)-phenyl]-5-(2,3,5,6-tetrahydro-[1,2']bipyrazinyl-4-yl)-pyrimidine-2,4,6-trione | 526 |
| 5 | 5-[4-(2-Chloro-phenoxy)-phenyl]-5-(4-pyrimidin-2-yl-piperazin-1-yl)-pyrimidine-2,4,6-trione | 492 |
| 6 | 5-[4-(2-Chloro-phenoxy)-phenyl]-5-(2,3,5,6-tetrahydro-[1,2']bipyrazinyl-4-yl)-pyrimidine-2,4,6-trione | 492 |
| 7 | 5-[4-(Phenoxy)-phenyl]-5-(4-pyrimidin-2-yl-piperazin-1-yl)-pyrimidine-2,4,6-trione | 458 |
| 8 | 5-[4-(Phenoxy)-phenyl]-5-(2,3,5,6-tetrahydro-[1,2']bipyrazinyl-4-yl)-pyrimidine-2,4,6-trione | 458 |
| 9 | 5-[4-(4-Methyl-phenoxy)-phenyl]-5-(4-pyrimidin-2-yl-piperazin-1-yl)-pyrimidine-2,4,6-trione | 472 |
| 10 | 5-[4-(4-Methyl-phenoxy)-phenyl]-5-(2,3,5,6-tetrahydro-[1,2']bipyrazinyl-4-yl)-pyrimidine-2,4,6-trione | 472 |
| 11 | 5-[4-(4-tert-Butyl-phenoxy)-phenyl]-5-(4-pyrimidin-2-yl-piperazin-1-yl)-pyrimidine-2,4,6-trione | 514 |
| 12 | 5-[4-(4-tert-Butyl-phenoxy)-phenyl]-5-(2,3,5,6-tetrahydro-[1,2']bipyrazinyl-4-yl)-pyrimidine-2,4,6-trione | 514 |
| 13 | 5-[4-(3,4-Dimethyl-phenoxy)-phenyl]-5-(4-pyrimidin-2-yl-piperazin-1-yl)-pyrimidine-2,4,6-trione | 486 |
| 14 | 5-[4-(3,4-Dimethyl-phenoxy)-phenyl]-5-(2,3,5,6-tetrahydro-[1,2']bipyrazinyl-4-yl)-pyrimidine-2,4,6-trione | 486 |
| 15 | 5-[4-(4-Bromo-phenoxy)-phenyl]-5-(4-pyrimidin-2-yl-piperazin-1-yl)-pyrimidine-2,4,6-trione | 537 |
| 16 | 5-[4-(4-Bromo-phenoxy)-phenyl]-5-(2,3,5,6-tetrahydro-[1,2']bipyrazinyl-4-yl)-pyrimidine-2,4,6-trione | 537 |

EXAMPLE 4

4-(4-5-[4-(4-Chloro-phenoxy)-phenyl]-2,4,6-trioxo-hexahydro-pyrimidin-5-yl-piperazin-1-yl)-N-(2-hydroxy-ethyl)-benzenesulfonamide A) N-(2-Hydroxy-ethyl)-4-piperazin-1-yl-benzenesulfonamide 4-Fluro-benzenesulfonylchloride was dissolved in dichloromethane (20 ml) and treated with a solution of ethanolamine (1.2 ml) in dichloromethane (10 ml). The mixture was stirred for 1 hour and extracted twice with water (50 ml). The water phase was saturated with sodium chloride and extracted twice with ethyl acetate. The combined organic phases were dried with magnesium sulfate and evaporated. 1.4 g of the resulting 4-fluoro-N-hydroxyethyl-benzenesulfonamide were dissolved in water (15 ml) and treated with piperazine (2.6 g). The mixture is refluxed for 6 hrs and kept at room temperature for 24 hrs. The precipitate was collected, washed with little water and dried to yield 1.6 g of the title compound identified by mass spectrometry (APCI [M+H]=286

B) 4-(4-5-[4-(4-Chloro-phenoxy)-phenyl]2,4,6-trioxo-hexahydro-pyrimidin-5-yl-piperazin-1-5-yl)-N-(2-hydroxy-ethyl)-benzenesulfonamride A solution of the compound from example 1 procedure G (230 mg) in methanol (5 ml) was treated with N-(2-Hydroxy-ethyl)-4-piperazin-1-yl-benzenesulfonamide (330 mg) (see above) The mixture was stirred for 24 hours. The residue obtained after evaporation of the reaction mixture was chromatographed on silica gel with methylenchloride/methanol (15%) as eluent. Pooling of the relevant fractions yields 186 mg of the title compound as an amorphous solid identified by mass spectroscopy: APCI [M+1]=614.

EXAMPLE 5

The following compounds were prepared using the procedures of example 1 substituting 4-chlorophenol with the corresponding phenols where needed. The piperazinederivatives were prepared according to example 4 procedure A and exchanging ethanolamine with the appropriate amine. The final products were identified by mass spectrometry.

| No. | Name | MS results APCI [M + H] |
|---|---|---|
| 1 | 4-4-[2,4,6-Trioxo-5-(4-phenoxy-phenyl)-hexahydro-pyrimidin-5-yl]-piperazin-1-yl-benzenesulfonamide | 536 |
| 2 | 4-4-[5-(4-Butoxy-phenyl)-2,4,6-trioxo-hexahydro-pyrimidin-5-yl]-piperazin-1-yl-benzenesulfonamide | 516 |
| 3 | 4-[4-(5-Biphenyl-4-yl-2,4,6-trioxo-hexahydro-pyrimidin-5-yl)-piperazin-1-yl]-benzenesulfonamide | 520 |
| 4 | N-(2-Hydroxy-ethyl)-4-4-[2,4,6-trioxo-5-(4-phenoxy-phenyl)- | 580 |

-continued

| No. | Name | MS results APCI [M + H] |
|---|---|---|
|  | hexahydro-pyrimidin-5-yl]-piperazin-1-yl-benzenesulfonamide | |
| 5 | N,N-Bis-(2-hydroxy-ethyl)-4-4-[2,4,6-trioxo-5-(4-phenoxy-phenyl)-hexahydro-pyrimidin-5-yl]-piperazin-1-yl-benzenesulfonamide | 624 |
| 6 | 4-(4-5-[4-(4-Bromo-phenoxy)-phenyl]-2,4,6-trioxo-hexahydro-pyrimidin-5-yl-piperazin-1-yl)-benzenesulfonamide | 615 |
| 7 | 4-(4-5-[4-(4-Bromo-phenoxy)-phenyl]-2,4,6-trioxo-hexahydro-pyrimidin-5-yl-piperazin-1-yl)-N-(2-dimethylamino-ethyl)-benzenesulfonamide | 686 |
| 8 | N-(2-Dimethylamino-ethyl)-4-[4-(5-octyl-2,4,6-trioxo-hexahydro-pyrimidin-5-yl)-piperazin-1-yl]-benzenesulfonamide | 551 |
| 9 | 4-(4-5-[4-(4-Chloro-phenoxy)-phenyl]-2,4,6-trioxo-hexahydro-pyrimidin-5-yl-piperazin-1-yl)-benzenesulfonamide | 570 |
| 10 | 4-(4-5[-4-(4-Chloro-phenoxy)-phenyl]-2,4,6-trioxo-hexahydro-pyrimidin-5-yl-piperazin-1-yl)-N,N-bis-(2-hydroxy-ethyl)-benzenesulfonamide | 658 |
| 11 | N-(2,3-Dihydroxy-propyl)-4-4-[2,4,6-trioxo-5-(4-phenoxy-phenyl)-hexahydro-pyrimidin-5-yl]-piperazin-1-yl-benzenesulfonamide | 610 |
| 12 | N-(2-Hydroxy-1-hydroxymethyl-ethyl)-4-4-[2,4,6-trioxo-5-(4-phenoxy-phenyl)-hexahydro-pyrimidin-5-yl]-piperazin-1-yl-benzenesulfonamide | 610 |
| 13 | N-2-[2-(2-Hydroxy-ethoxy)-ethoxy]-ethyl-4-4-[2,4,6-trioxo-5-(4-phenoxy-phenyl)-hexahydro-pyrimidin-5-yl]-piperazin-1-yl-benzenesulfonamide | 668 |
| 14 | 4-(4-5-[4-(4-Chloro-phenoxy)-phenyl]-2,4,6-trioxo-hexahydro-pyrimidin-5-yl-piperazin-1-yl)-N-(2,3-dihydroxy-propyl)-benzenesulfonamide | 644 |
| 15 | 4-(4-5-[4-(4-Chloro-phenoxy)-phenyl]-2,4,6-trioxo-hexahydro-pyrimidin-5-yl-piperazin-1-yl)-N-(2-hydroxy-1-hydroxymethyl-ethyl)-benzenesulfonamide | 644 |
| 16 | 4-(4-5-[4-(4-Chloro-phenoxy)-phenyl]-2,4,6-trioxo-hexahydro-pyrimidin-5-yl-piperazin-1-yl)-N-[2-(2-hydroxy-ethoxy)-ethyl]-benzenesulfonamide | 658 |
| 17 | 4-(4-5-[4-(4-Chloro-phenoxy)-phenyl]-2,4,6-trioxo-hexahydro-pyrimidin-5-yl-piperazin-1-yl)-N-2-[2-(2-hydroxy-ethoxy)-ethoxy]-ethyl-benzenesulfonamide | 702 |
| 18 | N-(2-Hydroxy-1,1-bis-hydroxymethyl-ethyl)-4,4-[2,4,6-trioxo-5-(4-phenoxy-phenyl)-hexahydro-pyrimidin-5-yl]-piperazin-1-yl-benzenesulfonamide | 640 |
| 19 | 4-(4-5-[4-(4-Chloro-phenoxy)-phenyl]-2,4,6-trioxo-hexahydro-pyrimidin-5-yl-piperazin-1-yl)-N-(2-hydroxy-1,1-bis-hydroxymethyl-ethyl)-benzenesulfonamide | 674 |

EXAMPLE 6

N-(2-Oxo-[1,3]dioxolan-4-ylmethyl)-4-4-[2,4,6-trioxo-5-(4-phenoxy-phenyl)-hexahydro-pyrimidin-5-yl]-piperazin-1-yl-benzenesulfonamide The product of example 5, no. 11 (120 mg) was dissolved in a mixture of dichloromethane (5 ml) and tetrahydrofurane (5 ml). The solution was treated with N,N'-carbonyldiimidazole (65 mg) and stirred for 4 hours at room temperature. The solvent was evaporated and the residue chromatographed on silica gel using dichloro-methane/methanol (9:1) as elution solvent. Evaporation of the product containing fractions yielded 60 mg of the title compound. mass spectrum: APCI [M+H]=636, [M−H]=634.

EXAMPLE 7

N-(4-Amino-butyryl)-4-4-[2,4,6-trioxo-5-(4-phenoxy-phenyl)-hexahydro-pyrimidin-5-yl]-piperazin-1-yl-benzenesulfonamide A) 4-(4-Benzyl-piperazin-1-yl)-benzenesulfonamide 4-Fluorobenzenesulfonylchloride (25 g) were dissolved in dichloromethane (250 ml) and treated at 0° C. with an aqueous solution of ammonia (25%, 50 ml). The mixture was stirred for 2 hours with cooling and overnight at room temperature. The reaction mixture was acidified and the organic solvent evaporated. The residue was extracted with ethyl acetate to yield 20 g 4-fluorobenzenesulfonamide, which were dissolved in water (300 ml), treated with 1-benzyl-piperazine (102 g) and refluxed for 24 hours. The reaction mixture was filtered to yield 26 g of the title compound. (mass spec APCI [M+H]=332)

B) 4-[4-(Piperazin-1-yl)-benzenesulfonylamino]-4-oxo-butyl-carbamic acid tert-butyl ester 4-(N-tert.-Butoxycarbonyl)-aminobutyric acid (3.05 g) was dissolved in tetrahydrofurane (30 ml) and treated with N,N'-carbonyldiimidazol (2.5 g). The mixture was stirred at room temperature for 15 minutes, heated under reflux for 15 minutes and stirred for 1 hour at room temperature. The product from step A (3.3 g) was added and the mixture was stirred overnight. The solvent was evaporated and the residue mixed with dichloromethane and water. The organic phase was separated, dried and the solvent evaporated. The residue was chromatographed on silica gel using dichloromethane/methanol (9:1) as eluting solvent. The product was subjected to catalytic hydrogenation in methanol using Pd on carbon to yield 2.5 g of the title compound. (mass spec APCI [M−H]=425).

C) N-(4-Amino-butyryl)-4-4-[2,4,6-trioxo-5-(4-phenoxy-phenyl)-hexahydro-pyrimidin-5-yl]-piperazin-1-yl-benzenesulfonamide The product obtained in procedure B was reacted analogously to example 1 procedure H with 5-bromo 5-(4-

(phenoxy)-phenyl)-pyrimidine-2,4,6-trione. The latter compound was prepared analogously to the procedures described in example 1 substituting the p-chloro-phenol with phenol. To remove the BOC-protecting group the product (290 mg) was dissolved in a 4 N solution of HCl in dioxane. After 1 hour at room temperature the solution was decanted and the residue triturated with ether to yield 180 mg of the title compound. (mass spectrum APCI [M+H]=621).

EXAMPLE 8

The following compounds were prepared using the procedures of example 7 substituting 4-(N-tert.butoxycarbonyl)-amino-butyric acid with the appropriate N-tert.butoxycarbonyl protected amino acid. The final products were identified by mass spectrometry.

proteolytic cleavage of the substrate therefore was measured by the fluorescence value.

a) First Method

The assay was performed at 25° C. in a freshly prepared 50 mM Tris buffer (pH 8.0) treated with dithiozone to remove traces of heavy metals. 4 mM $CaCl_2$ was added and the buffer saturated with argon. Stock solutions of adamalysin II were prepared by centrifugation of the protein from an ammonium sulfate suspension and subsequent dissolution in the assay buffer. Stock solutions of collagenase were diluted with the assay buffer. Enzyme concentrations were determined by uv measurements ($\epsilon_{280}$=2.8 $10^4$ $M^{-1}$ $cm^{-1}$, $\epsilon_{288}$: 2.2 $10^4$ $M^-$. $cm^{-1}$) and the stock solutions were stored in the cold. This solution was diluted 1:100 to obtain the final 16 nM assay concentration. The fluorogenic substrate DNP-Pro-Leu-Gly-Leu-Trp-Ala-D-Arg-$NH_2$ with a $K_m$ of

| No. | Name | MS results APCI [M + H] |
|---|---|---|
| 1 | N-Aminoacetyl-4-4-[2,4,6-trioxo-5-(4-phenoxy-phenyl)-hexahydro-pyrimidin-5-yl]-piperazin-1-yl-benzenesulfonamide | 593 |
| 2 | N-(5-Amino-pentanoyl)-4-4-[2,4,6-trioxo-5-(4-phenoxy-phenyl)-hexahydro-pyrimidin-5-yl]-piperazin-1-yl-benzenesulfonamide | 635 |
| 3 | N-(5-Amino-pentanoyl)-4-(4-5-[4-(4-chloro-phenoxy)-phenyl]-2,4,6-trioxo-hexahydro-pyrimidin-5-yl-piperazin-1-yl)-benzenesulfonamide | 669 |
| 4 | N-(4-Amino-butyryl)-4-(4-5-[4-(4-chloro-phenoxy)-phenyl]-2,4,6-trioxo-hexahydro-pyrimidin-5-yl-piperazin-1-yl)-benzenesulfonamide | 655 |

EXAMPLE 9

2-Oxo-2-(4-4-[2,4,6-trioxo-5-(4-phenoxy-phenyl)-hexahydro-pyrimidin-5-yl]-piperazin-1-yl-benzenesulfonylamino)-ethyl]-carbamic acid 4-methoxy-phenyl ester The product of example 5 no. 1 (140 mg) was dissolved in dichloromethane (10 ml), mixed with triethylamine (0.14 ml) and treated with 4-methoxyphenylchloroformate. The mixture was stirred for 90 minutes at room temperature and evaporated. The residue was chromatographed on silica gel using dichloromethane/methanol (9:1) as eluent. Pooling of the relevant fractions yielded 90 mg of the title compound. (Mass spec APCI [M+H]=743).

EXAMPLE 10

In order to determine the inhibition of MMPs, for example HNC (MMP-8), the catalytic domain (isolation and purification see for example Schnierer, S., Kleine, T., Gote, T., Hillemann, A., Knäuper, V., Tschesche, H.,Biochem. Biophys. Res. Commun. (1993) 191, 319–326) were incubated with inhibitors having various concentrations. Subsequently, the initial reaction rate in the conversion of a standard substrate was measured in a manner analogous to Grams F. et al., FEBS 335 (1993) 76–80).

The results awee evaluated by plotting the reciprocal reaction rate against the concentration of the inhibitor. The inhibition constant (Ki) is obtained as the negative section of the abscissis by the graphical method according to Dixon, M., Biochem. J. (1953) 55, 170–202.

The synthetic collagenase substrate was a heptapeptide which is coupled, at the C terminus, with DNP (dinitrophenol). Said DNP residue quenched by steric hindrance the fluorescence of the adjacent tryptophane of the heptapeptide. After cleavage of a tripeptide which includes the DNP group, the tryptophane fluorescence increased. The 52 $\mu$M was used at a concentration of 21.4 $\mu$M; for the $K_i$ determination a 12.8 $\mu$M concentration has also been used. Substrate fluorescence was measured at an excitation and emission wavelength of $\lambda$=320 and 420 nm, respectively, on a spectrofluorimeter (Perkin Elmer, Model 650-40) equipped with a thermostated cell holder. Substrate hydrolysis was monitored for 10 minutes. immediately after adding the enzyme. All reactions were performed at least in triplicate. The $K_i$ values-of the inhibitors were calculated from the intersection point of the straight lines obtained by the plots of $v_o/v_i$ vs. [concentration of inhibitor], whereas $IC_{50}$ values were calculated from plots of $v_i/v_o$ [concentration of inhibitor] by non-linear regression with simple robust weighting.

b) Second Method

Assay buffer:

50 mM Tris/HCl pH 7.6 (Tris=Tris-(hydroxymethyl)-aminomethan)

100 mM NaCl/10 mM CaCl2/5% MeOH (ff necessary)

Enzyme: 8 nM catalytic domain (Met80-Gly242) of human neutrophil collagenase (MMP-8)

Substrate:

10 microM DNP-Pro-Leu-Gly-Leu-Trp-Ala-D-Arg-NH2

Total assay volume:

1 ml

A solution of the enzyme and inhibitor in assay buffer (25° C.) was prepared. The reaction was started by giving the substrate into the solution. The cleavage of the fluorogenic substrate was followed by fluorescence spectroscopy with an excitation and emission wavelength of 280 and 350 nm, respectively. The $IC_{50}$ value was calculated as the inhibitor concentration, which is necessary to decrease the velocity of the reaction to the half in comparison to the reaction without inhibitor.

Table 1 shows the $IC_{50}$ values found in comparison with the compounds from example 26 and preferred compound no. 118 cited in the patent application EP0869947

TABLE 1

IC$_{50}$ Values of MMP-Inhibitor (vs. MMP-8, catalytic domain)

| | IC$_{50}$ [nM] |
|---|---|
| Reference Compound from EP0869947 | |
| preferred no. 118 | 60 |
| example 26 | 15 |
| Compounds from this invention | |
| Example 1 | 10 |
| Example 2 | 4 |
| Example 3 - no. 1 | 4 |
| Example 3 - no. 2 | 2 |
| Example 3 - no. 15 | 4 |
| Example 3 - no. 15 | 4 |
| Example 4 | 10 |
| Example 5 - no. 6 | 2.8 |
| Example 5 - no. 7 | 13 |
| Example 5 - no. 9 | 12 |
| Example 5 - no. 10 | 9 |
| Example 5 - no. 11 | 4.5 |
| Example 5 - no. 12 | 5.5 |
| Example 5 - no. 13 | 6 |
| Example 5 - no. 18 | 13 |
| Example 5 - no. 19 | 9 |
| Example 6 | 9 |

What is claimed is:

1. A compound of formula

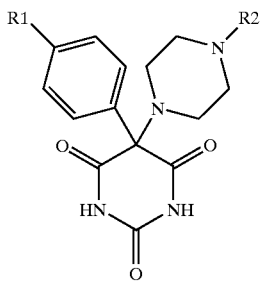

(I)

in which

R$_1$ is a phenyl, phenoxy, phenylthio, phenylsulfinyl, phenylsulfonyl, phenylamino or phenylmethyl residue, wherein the phenyl moiety is unsubstituted or substituted by one or more halogen atoms, hydroxy, C$_1$–C$_6$ alkoxy, C$_1$–C$_6$ alkyl, cyano or nitro groups, and R$_2$ is an phenyl substituted by —SO$_2$NR$_3$R$_4$, wherein R3 and R4, are the same or different, and are C$_1$–C$_6$ alkyl, straight or branched, which is unsubstituted or substituted by one or more groups selected from OH, and N(CH$_3$)$_2$, or which is interrupted by oxygen, or are CO—R$_5$, wherein R$_5$ is an alkyl group which is unsubstituted or substituted by NH$_2$, or a pharmaceutically acceptable salt thereof.

2. The compound of claim 1, wherein R$_1$ is phenoxy wherein the phenyl moiety is unsubstituted or substituted by one or more halogen atoms, hydlroxy, C$_1$–C$_6$ alkoxy, C$_1$–C$_6$ alkyl, cyano or nitro groups.

3. A compound of claim 2, wherein R$_1$ is phenoxy substituted by one or more chlorine, bromine, methyl or tert. Butyl groups.

4. A compound of claim 1, wherein R$_3$ represents hydrogen and R$_4$ represents hydrogen, —CH$_2$CH$_2$OH; —CH$_2$CH$_2$—N(CH$_3$)$_2$; —CH$_2$—CH(OH)—CH$_2$OH; —CH—(CH$_2$OH)$_2$; —CH$_2$—CH$_2$—O—CH$_2$CH$_2$—O—CH$_2$CH$_2$OH; or —C(CH$_2$OH)$_3$.

5. A compound of formula

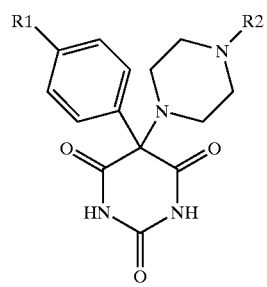

(I)

in which

R$_1$ is a phenyl, phenoxy, phenylthio, phenylsulfinyl, phenylsulfonyl, phenylamino or phenylmethyl residue, wherein the phenyl moiety is substituted by one or more halogen atoms, hydroxy, C$_1$–C$_6$ alkoxy, C$_1$–C$_6$ alkyl, cyano or nitro groups, and R$_2$ is a pyrimidine pyrazine or its N-oxides, or a pharmaceutically acceptable salt thereof.

6. The compound of claim 5, wherein R$_1$ is phenoxy substituted by one or more halogen atoms, -hydroxy, C$_1$–C$_6$ alkoxy, C$_1$–C$_6$ alkyl, cyano or nitro groups.

7. A compound of claim 6, wherein R$_1$ is phenoxy substituted by one or more chlorine, bromine, methyl or tert. Butyl groups.

8. The compound 5-(4-(4-Chloro-phenoxy)-phenyl)-5-(4pyrimidine2-yl-piperazine)-pyrimidine-2,4,6-trione.

9. The compound 5-[4-(4-Chloro-phenoxy)-phenyl]-5-(2,3,5,6-tetrahydro-[1,2']bipyrazinyl-4-yl)-pyrimidine-2,4,6-trione.

10. The compound 5-[4-(3,4-Dichloro-phenoxy)-phenyl]-5-(4-pyrimidin-2-yl-piperazin-1-yl)-pyrimidine-2,4,6-trione.

11. The compound 5-[4-(3,4-Dichloro-phenoxy)-phenyl]-5-(2,3,5,6-tetrahydro-[1,2']bipyrazinyl-4-yl)-pyrimidine-2,4,6-trione.

12. The compound 5-[4-(4-Bromo-phenoxy)-phenyl]-5-(4-pyrimidin-2-yl-piperazin-1-yl)-pyrimidine-2,4,6-trione.

13. The compound 4-(4-5-[4-(4-Chloro-phenoxy)-phenyl]-2,4,6-trioxo-hexahydro-pyrimidin-5-yl-piperazin-1-yl)-N-(2-hydroxy-ethyl)-benzenesulfonamide.

14. The compound 4(4-5-[4-(4-Bromo-phenoxy)-phenyl]-2,4,6-trioxo-hexahydro-pyrimidin-5-yl-piperazin-1-yl)-benzenesulfonamide.

15. The compound 4-(4-5-[4-(4-Bromo-phenoxy)-phenyl]-2,4,6-trioxo-hexahydro-pyrimidin-5-yl-piperazin-1-yl)-N-(2-dimethylamino-ethyl)-benzenesulfonamide.

16. The compound 4-(4-5-[4-(4-Chloro-phenoxy)-phenyl]-2,4,6-trioxo-hexahydro-pyrimidin-5-yl-piperazin-1-yl)-benzenesulfonamide.

17. The compound 4-(4-5-[4-(4-Chloro-phenoxy)-phenyl]-2,4,6-trioxo-hexahydro-pyrimidin-5-yl-piperazin-1-yl)-N,N-bis-(2-hydroxy-ethyl)-benzenesulfonamide.

18. The compound N-(2,3-Dihydroxy-propyl)-4-4-[2,4,6-trioxo-5-(4-phenoxy-phenyl)-hexahydro-pyrimidin-5-yl]-piperazin-1-yl-benzenesulfonamide.

19. The compound N-(2-Hydroxy-1-hydroxymethyl-ethyl)-4-4-[2,4,6-trioxo-5-(4-phenoxy-phenyl)-hexahydro-pyrimidin-5-yl]-piperazin-1-yl-benzenesulfonamide.

20. The compound N-2-[2-(2-Hydroxy-ethoxy)-ethoxy]-ethyl-4-4-[2,4,6-trioxo-5-(4-phenoxy-phenyl)-hexahydro-pyrimidin-5-yl]-piperazin-1-yl-benzenesulfonamide.

21. The compound N-(2-Hydroxy-1,1-bis-hydroxymethyl-ethyl)-4-4-[2,4,6-trioxo-5-(4-phenoxy-phenyl)-hexahydro-pyrimidin-5-yl]-piperazin-1-yl-benzenesulfonamide.

22. The compound 4-(4-5-[4-(4-Chloro-phenoxy)-phenyl]-2,4,6-trioxo-hexahydro-pyrimidin-5-yl-piperazin-1-yl)-N-(2-hydroxy-1,1-bis-hydroxymethyl-ethyl)-benzenesulfonamide.

23. The compound N-(2-Oxo-[1,3]dioxolan-4-ylmethyl)-4-4-[2,4,6-trioxo-5-(4-phenoxy-phenyl)-hexahydro-pyrimidin-5-yl]-piperazin-1-yl-benzenesulfonamide.

* * * * *

UNITED STATES PATENT AND TRADEMARK OFFICE
CERTIFICATE OF CORRECTION

PATENT NO.   : 6,498,252 B1
DATED        : December 24, 2002
INVENTOR(S)  : Frank Grams et al.

It is certified that error appears in the above-identified patent and that said Letters Patent is hereby corrected as shown below:

Column 14,
Line 28, "-hydroxy" should be -- hydroxy --
Line 35, "(4pyrimidine2-yl-" should be -- (4-pyrimidine-2-yl- --

Signed and Sealed this

Fifteenth Day of July, 2003

JAMES E. ROGAN
*Director of the United States Patent and Trademark Office*